United States Patent [19]

Mattingly

[11] Patent Number: 4,608,047
[45] Date of Patent: Aug. 26, 1986

[54] SANITARY NAPKIN ATTACHMENT MEANS
[75] Inventor: William B. Mattingly, Somerset, N.J.
[73] Assignee: Personal Products Company, Milltown, N.J.
[21] Appl. No.: 737,755
[22] Filed: May 28, 1985
[51] Int. Cl.$^4$ ............................................. A61F 13/16
[52] U.S. Cl. .................................................. 604/387
[58] Field of Search ............... 604/387, 386, 385, 389, 604/391, 400, 401

[56] References Cited
U.S. PATENT DOCUMENTS
4,285,343 8/1981 McNair ............................... 604/387

Primary Examiner—John D. Yasko
Attorney, Agent, or Firm—Jason Lipow

[57] ABSTRACT

This invention provides a sanitary napkin of the type emplacement in the inner crotch portion of an undergarment. The napkin comprises a central absorbent element having flaps extending from each of its longitudinal edges. The flaps extend to a sufficient length to allow the flaps to overlie the outer crotch portion of an undergarment with the flaps being sufficiently drapable so as to allow each to fold about the crotch portion at any of an infinite number of lines lying essentially parallel to the junction line between the absorbent element and each flap. Accordingly, when the sanitary napkin is applied to crotch portions of varying width, the napkin will conform to the dimensions of the crotch and be emplaced without wrinkling.

18 Claims, 13 Drawing Figures

SANITARY NAPKIN ATTACHMENT MEANS

BACKGROUND OF THE INVENTION

This invention relates to an absorbent product for absorbing body fluids and in particular, to such a product to be worn against the perineal portion of the body and held in place by attachment to the crotch portion of the undergarment worn by the user. Such products are now in wide use as sanitary napkins, panty shields, panty liners and adult incontinence pads. While this invention is directed to all such products, for purposes of simplification, these products will be referred to herein simply as napkins.

Typically, these napkins comprise a generally elongated absorbent element such as a pad of absorbent material, having a body facing side, a garment facing side, longitudinally extending edges and lateral ends. The element is usually provided with a body fluid pervious cover on the body facing side and a body fluid impervious cover on the garment facing side which latter cover may be exposed or may be provided with a further overlying layer. These prior products are held in place by providing an area or areas of pressure sensitive adhesive on the garment facing side to adhere to the inner crotch surface of the wearer's undergarment. A great number of suggestions and patents exist which suggest varying configurations of pressure sensitive adhesive applications in such products. Examples of such suggestions are found in U.S. Pat. Nos. 3,913,580; 3,897,783 and 3,888,255.

While in the main, such prior products have performed well, remaining in place and providing the user with ease of placement and removal, these products have suffered from certain drawbacks. For example, the inner crotch surface to which these products are adhered is constantly being distorted, twisted and stretched due to the movements of the wearer. As a result, frequently, the adhesive attachment detaches with the undesirable result of the napkin's moving out of place. Further, while the napkin frequently reattaches owing to the continuing adhesive nature of the pressure sensitive adhesive, reattachment often places the napkin in an undesirable position wherein the napkin does not function properly. In an extreme case, detachment of the adhesive also results in the adhesive folding over on itself and then becoming unavailable for reattachment.

Further, it has been discovered that, in the event that the inner crotch becomes moist for one reason or another, the adhesive attachment is greatly weakened and misplacement of the napkin results.

Still another drawback related to prior napkins occurs. It has been discovered that often, in the course of wearing a napkin, the edges of the crotch of the panty tends to enfold onto the body facing surface of the napkin. In such a position, the panty is likely to be wetted with body fluid, either emanating from the napkin or deposited from the body itself.

This latter problem has been addressed to some degree in U.K. Pat. No. 2 048 684 wherein a sanitary towel has been provided with flaps extending along the longitudinal edges of the absorbent element. These flaps appear to protect portions of the inner crotch of the undergarment adjacent to the absorbent element but do not provide any means for avoiding fold over of the panty. Nor does the U.K. Pat. in any way address the problems of attachment outlined above.

Accordingly, there is a need for a more protective sanitary napkin having an improved attachment means.

SUMMARY OF THE INVENTION

I have discovered that the above-outlined problems associated with the prior art products may be obviated and a sanitary napkin may be provided with an improved means for attachment. Specifically, my invention is directed toward an improvement in a sanitary napkin for placement in the inner crotch portion of an undergarment which napkin has an absorbent element having a body facing side, a garment facing side, longitudinally extending edges and transverse ends. The improvement comprises providing flaps, extending from each longitudinal side. The flaps extend to a length sufficient to allow the flaps to overlie the outer crotch portion of the undergarment. Preferably, the flaps extend to a degree sufficient to allow a portion thereof to overlap each other in the area in which they overlie the outer crotch portion of the undergarment. In a preferred embodiment, the flaps are provided with means for securing them in place with portions thereof overlying the outer crotch portion of the undergarment. Such means may be pressure sensitive adhesive and may be provided so that the flaps can adhere to each other in the area where they overlap or to the outer crotch portion of the undergarment or both. Alternative means to pressure sensitive adhesive may be employed such as cohesive materials or the hook and loop fasteners sold uner the trademark "Velcro" by Velcro USA, Inc.

It will be understood that the attachment system may be supplemented by providing additional adhesive to the garment facing side of the product for adhering the product to the inner surface of the crotch portion of the undergarment, as well as utilizing the flap attachment system.

The attachment system has obviated prior art napkin drawbacks. By encircling the crotch portion with the attachment flaps, the encircled portion of the undergarment tends to move together with the napkin and hence maintains their relative positions such that even if they move with the user's normal motion, they will return together in the proper position. Still further, the encircling flaps prevent the edges of the crotch from folding over onto the face of the napkin and hence becoming wet.

Still another advantage accrues. It has been discovered that frequently, in conventional napkins, body fluid deposited on the napkin escapes the absorbent element at the longitudinal sides thereof and wets the crotch of the undergarment. This situation arises most often due to either a sudden surge of deposited fluid which exceed the rate of fluid take-up by the pad, or because the napkin is out of position or fully saturated in a local area of fluid disposition. For what ever reason such can occur, wetting of the undergarment is precluded by the napkin of this invention in that the flaps overlie the portions of the crotch adjacent to the longitudinal sides of the napkin. Preferably, the flaps are comprised of a material which is impervious to body fluid and hence will prevent such escaped fluid from wetting the crotch portion. In a preferred embodiment, the impervious flaps are covered, at least on a portion of the body facing side of the flaps closest to the absorbent element, with body fluid absorbing material, so that escaped fluid may be absorbed and prevented from flowing across the flaps and onto the body or garments of the wearer.

It will be understood that one major advantage of the invention is that when properly emplaced on the crotch portion of an undergarment, the garment side of the absorbent element of the napkin tends to lie smoothly against the crotch portion and, hence, moves together with the garment as the wearer moves. In order to do this, it is essential that the napkin conform to the varying sizes of undergarments rather than force the undergarment to bunch or wrinkle in an attempt to conform to the napkin. It is important, then, that the flap be drapable enough so as to fold about the crotch portion at any of the infinite number of lines which lie approximately parallel to the longitudinal direction of the absorbent element and between the junction line of the element and the flaps and the extreme end of the flaps. If, instead, a line exists along this transverse length of flap which is capable of acting as a hinge in a relatively less drapable flap, then the edge of the crotch portion of an undergarment will be biased to engage this hinge and the crotch will adapt in width to the spacing between hinges in each of the flaps rather than the napkin adapting to the width of the crotch portion, as is required.

In still another embodiment of this invention, the napkin is packaged in a folded condition whereby essentially only the garment facing side of the napkin is exposed. Upon using the napkin, the same folding may be accomplished, so as to facilitate clean disposal of the product.

DETAILED DESCRIPTION OF THE INVENTION

Figure 1:
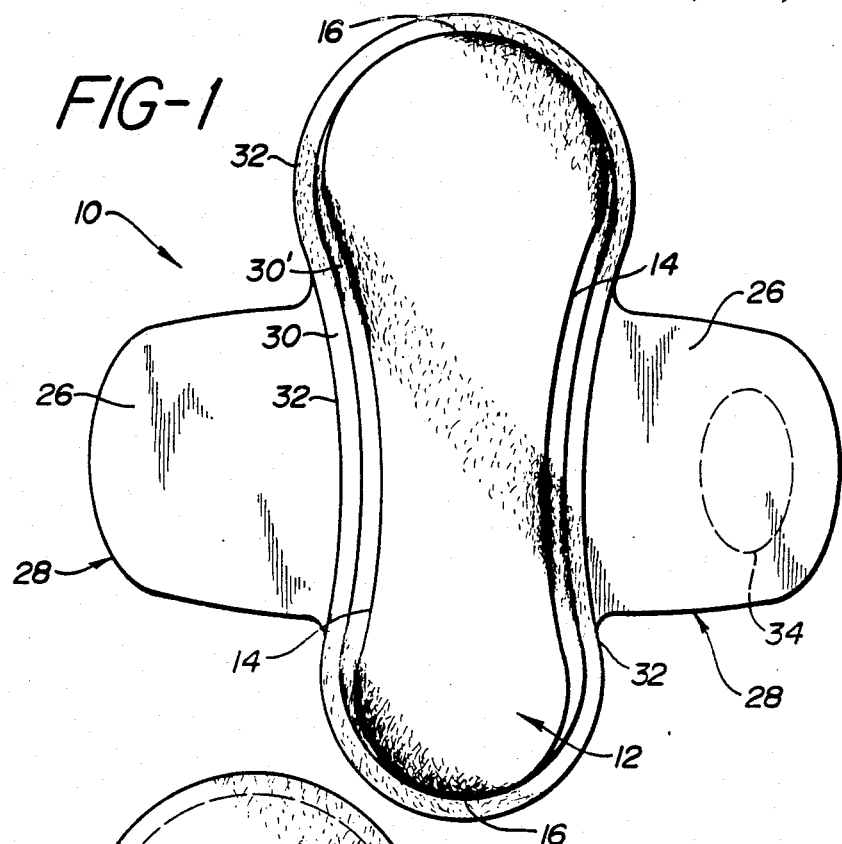
FIG. 1 is a plan view of the body facing side of an embodiment of this invention.
Figure 2:
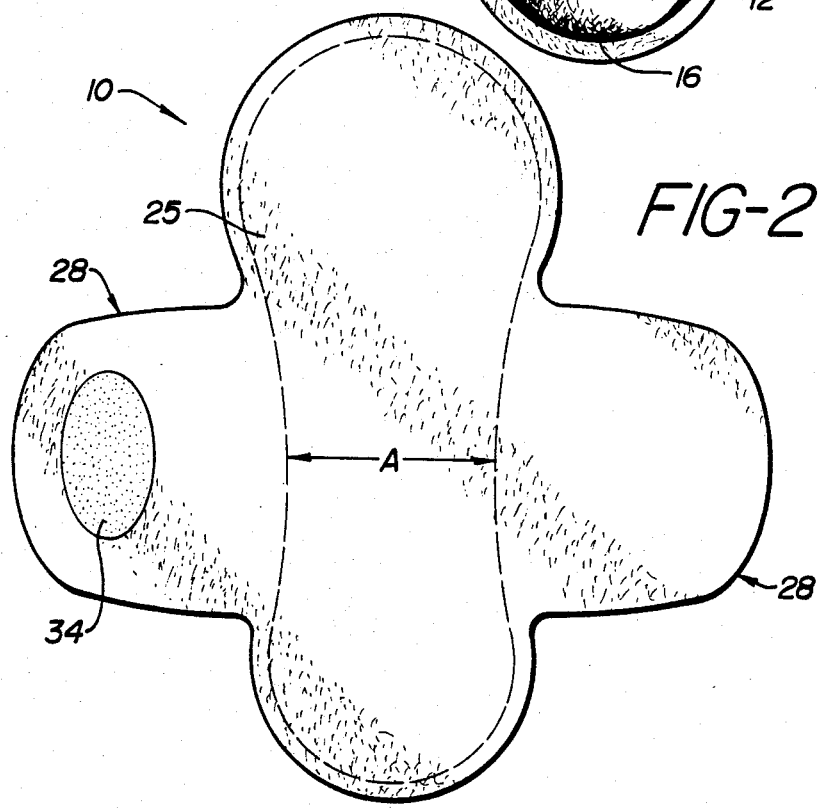
FIG. 2 is a plan view of the garment facing side of the napkin of FIG. 1.

Referring now to the drawings, FIGS. 1 and 2 are plan views of the body facing side and garment facing side, respectively, of a sanitary napkin 10 embodying this invention.

The napkin 10 is provided with a centrally located absorbent element 12 illustrated in what may be termed an "hourglass shape" and having generally longitudinally extending edges 14 and transversely extending ends 16. The absorbent element 12 may be comprised of any of the well known absorbent materials used in products for absorbing body fluids such as, for example, loosely associated absorbent hydrophilic material such as cellulose fibers, e.g. wood pulp, regenerated cellulose or cotton fibers. Such fibers may be chemically or physically modified and the absorbent element may include such fibers in combination with other materials, both natural and synthetic, such as hydrophilic foams, hydrophilic polymers or the like. Wood pulp is frequently the material of choice primarily because it is inexpensive and readily available.

Figure 5:
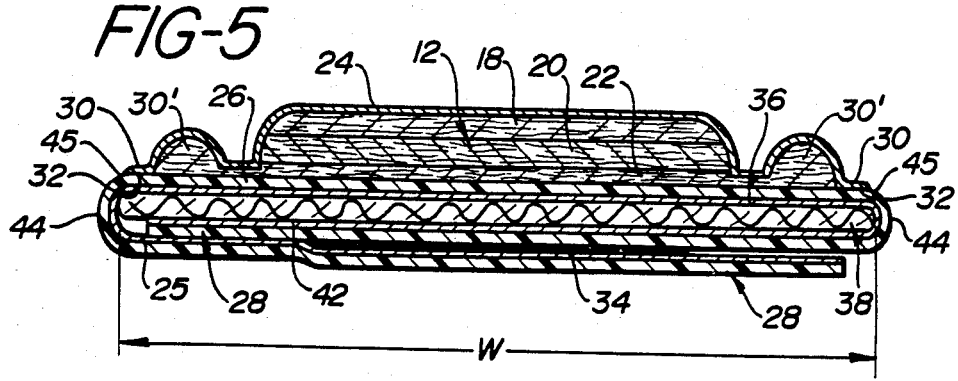
FIG. 5 is a cross-sectional view of the secured napkin of FIG. 4 taken through line 5—5.

The absorbent element may also comprise layers of materials which in the aggregate are body fluid absorbent. For example the outermost layer (closest to the body) may be a resilient, relatively non-absorbing, fluid pervious material. Such a material is provided for comfort and conformability and directs fluid to an underlying layer, e.g. wood pulp, which retains such fluid. As useful material for this outer layer is comprised of hollow polyester fibers having a denier of about 8.5 and a length of about 1.5 inches. FIG. 5, a cross-sectional view of the napkin 10 secured to an undergarment, illustrates this construction wherein the absorbent element 12 comprises a resilient layer 18 and an absorbent layer 20.

Underlying absorbent element 12 is another layer of absorbent material 22 to provide additional resiliency to the product. As best viewed in FIGS. 1 and 5 this absorbent material 22 extends beyond the longitudinally extending edges 14 of absorbent element 12 and this extension is provided to entrap any body fluid which escapes from the sides of element 12. The absorbent material 22 should extend a sufficient degree beyond the edges 14 so as to protect the inner crotch portion of the wearer's undergarment. Such width does not necessarily have to be as wide as the width of the undergarment crotch, but is preferably at least as wide as a major portion thereof. Thus, the dimension A shown in FIG. 2 should be at least about 1.0 inches wide and, preferably, at least about 1.5 inches wide. Needless to say, absorbent material 22 may be substantially wider and, in fact, may extend to the very edges of the flaps and even be coextensive therewith.

Absorbent material 22 may comprise a thin, absorbent layer of material such as tissue, fabric or the like made of cellulosic fibers. Because such material is provided as a safety measure and is only required to retain escaped fluid, it need not be very absorbent at all and, in fact, may be comprised of any capillary or cellular system including hydrophobic material. Thus, a useful material may be a fabric comprised of the hollow polyester fibers and heat bondable polyester/polyethylene conjugate fibers. Such conjugate fibers are fibers which comprise a polyester core surrounded by a sheath of polyethylene. Preferably, the conjugate fibers employ high density polyethylene, that is, linear polyethylene that has a density of at least 0.94 gm/cc and a Melt Index (as determined by ASTMD-1288E method, employing the parameters of 190° C. and 2160 gms.) of greater than 1, preferably greater than about 10, and more preferably about 40 to about 60 percent, by weight polyester and, preferably, from 45 to 55 percent by weight polyester, with the remainder being polyethylene. Such fibers may be used in deniers of from 1 to about 6 and may be from about ½ inch (1.27 cm.) to about 3 to 4 inches (7.62 to 10.16 cm.) long. The fabric comprising such fibers is stabilized by applying heat thereto whereby thermal bonding takes place. This fabric has the added advantage of providing resiliency and conformability to the product.

As best viewed in FIG. 5, overlying the absorbent element 12 and preferably also the absorbent material 22 is a fluid permeable cover material 24. This cover may comprise any of the well known cover materials used in sanitary napkins including, for example, non-woven fabrics of cellulose, regenerated cellulose, polyester or other synthetic polymers. Additionally, polymeric fibers having apertures therethrough to render the films pervious to fluids may also be employed. A cover material of choice is a fabric comprising the same heat bondable polyester/polyethylene conjugate fibers as are described above, but without the hollow polyester fibers preferably employed for layer 22.

Underlying the garment facing surface of absorbent element 12 is a body fluid impervious barrier 26 provided to preclude body fluid from passing onto the undergarment of the wearer. Barrier 26 may be any polymeric film such as polyethylene, polypropylene, or cellophane or may be a normally fluid-pervious material that has been treated to be impervious such as a fluid repellent paper.

In accordance with the teachings of this invention, flaps 28 are provided extending from each of the longitudinal edges 14 of absorbent element 12. As will be come apparent from the further description, flap 28 extended a sufficient degree to enable the flap to overlie the outer crotch portion of the wearer's undergarment. Flaps 28 are provided for two primary purposes, namely: to more fully protect the user's undergarment from liquid escaping from the absorbent element 12 at longitudinal edges 14 and to act as an attachment system to hold the absorbent element 12 firmly in place and have element 12 move together with the crotch of the garment as the latter moves responsive to the wearer's movements.

To provide protection for the user's undergarment, it is, of course, important that flaps 28 comprise a layer of fluid impervious barrier material such as these described in connection with barrier 26. In fact, in the preferred embodiment of this invention and as illustrated in the drawings, flaps 28 are no more than appropriately shaped extensions of barrier 26. In a preferred embodiment, the impervious material comprising the flaps 28 is covered, particularly at the portion of the flap adjacent to the absorbent element 12, with body fluid absorbing material 30, 30'. This material is provided so that escaped fluid from the element 12 may be absorbed and prevented from flowing across the flaps and onto the body or garment of the wearer. In the specific embodiment shown in FIGS. 1, 2 and 5, this absorbent material is in two parts with material 30 being no more than an extension of cover 24 and material 30' being an extension of layer 22. It should be noted that neither of these materials are made up of hydrophilic fibers but instead have sufficient capillary to retain the small quantities of escaped liquid and, hence, are "absorbent". Materials which are hydrophilic, e.g., cellulosic fiber fabrics, may also be employed for this purpose. It should also be understood that while such materials are illustrated as extending onto flaps 28 for only a short distance from element 12, if desired the material may extend even further toward the end of flap 28 and even to the degree that they are coextensive with flap 28. Advantageously, by employing a thermoplastic material for cover 24 and using this as absorbent material 30 in conjunction with a thermoplastic barrier flap 28, the entire product may be stabilized and sealed with a peripheral heat seal 32. It will be understood that the choices described above in connection with the construction of the flaps are all to be made within the contraint that the flaps must be sufficiently drapable so as to allow the napkin to conform to undergarments having varying crotch widths as shall be further explained below.

Figure 3:
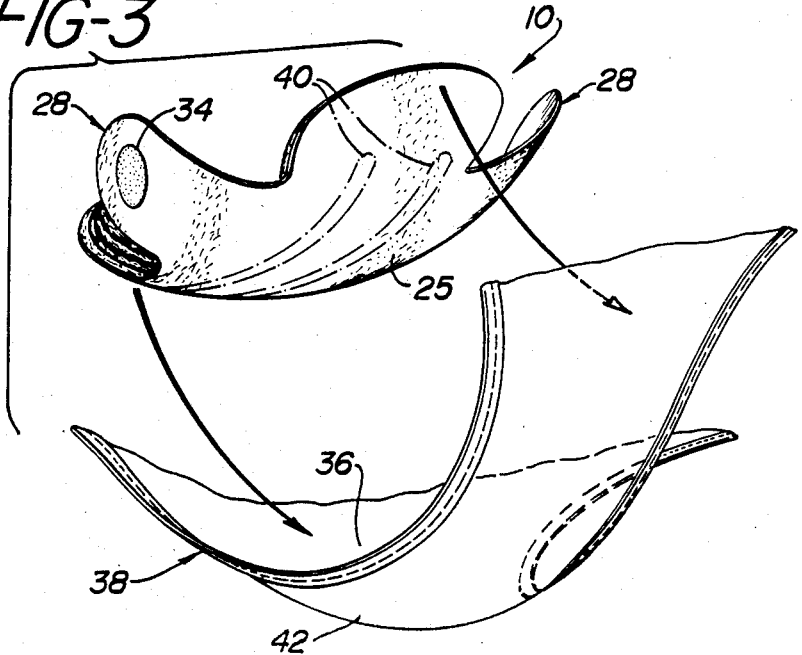
FIG. 3 is a perspective, schematic illustration of the placement of the napkin of FIG. 1 onto the inner crotch portion of an undergarment.
Figure 4:
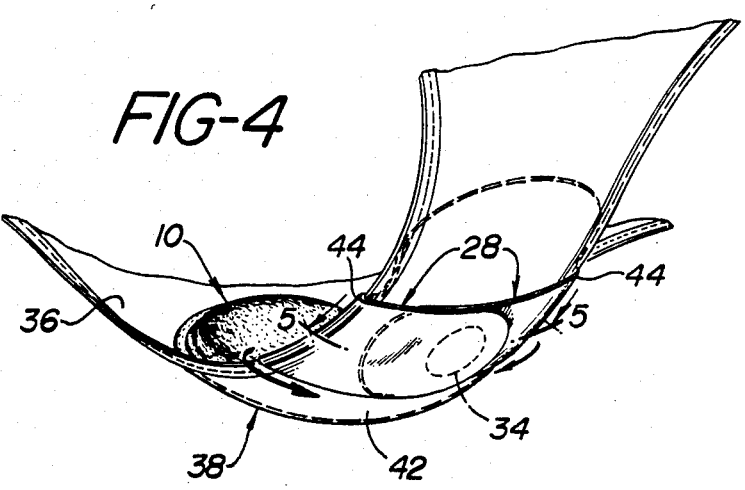
FIG. 4 is a perspective, schematic illustration of the napkin of FIG. 1 being secured to the crotch by having the flaps folded upon the outer crotch portion of an undergarment.
Figure 10:
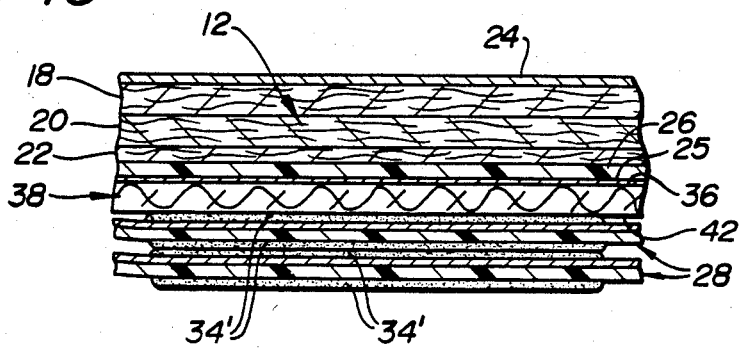
FIG. 10 is a partial cross-sectional view of another embodiment of the napkin of this invention, analogous to a partial view of FIG. 5.
Figure 11:
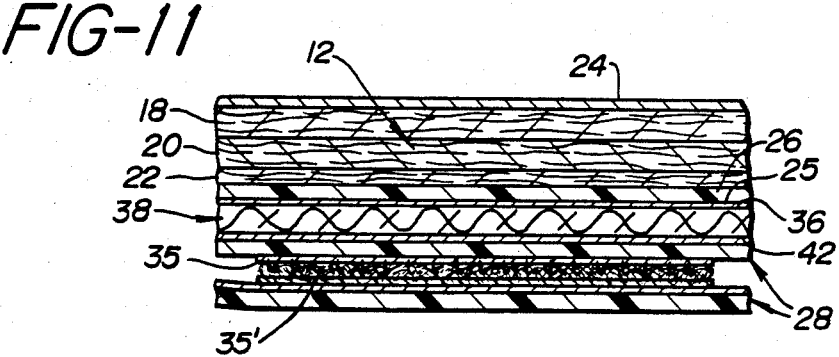
FIG. 11 is a partial, cross-sectional view of still another embodiment of the napkin of this invention, analogous to a partial view of FIG. 5.

As best viewed in FIG. 2, a plan view of the garment facing side of napkin 10, one flap (left hand flap in FIG. 2) is provided with an adhesive element 34 in the form of an oval area, as a means for affixing the flaps 28 to the outer crotch portion of the undergarment. It will be understood that alternative shapes, e.g., lines, squares, etc., may also be employed. FIGS. 3-5 best illustrate this means for affixing the napkin in place. In FIG. 3, an exploded perspective view, the napkin in emplaced into the inner crotch portion 36 of undergarment 38. To aid in holding the absorbent element 12 firmly against the inner crotch portion 36, pressure-sensitive adhesive lines 40 (shown in phantom lines in FIG. 3) may be employed, as is well known in connection with prior art napkins. The employment of the napkin into the inner crotch portion is best accomplished by employing the napkin while the user's undergarment is in a lowered position. Once the napkin is firmly emplaced in the inner crotch portion, the flaps 28 are then to be folded about the crotch portion so as to overlie the outer crotch portion 42 of the undergarment and be secured in such position. This step is best accomplished by the user raising the undergarment into its normal wearing position and then folding the flaps about the outer crotch portion. As is best illustrated in FIGS. 4 and 5, in this specific embodiment illustrated in these figures, the flaps 28 are folded along fold lines 44 to overlie outer crotch portion 42. In this embodiment the flaps overlap each other as they overlie outer crotch portion 42 and the adhesive element 34 is so placed as to be in the area of the overlap. Accordingly, the adhesive element 34 serves to hold the napkin in place by adhering one flap to the other. This configuration has the advantage that adhesion of the flap directly to the fabric of the undergarment is avoided and the problem of adhesive residue being left on the panty fabric is likewise avoided. To take advantage of this feature, the flaps must be folded in a particular order, i.e. non adhesive-bearing flap followed by adhesive bearing flap, and such requirement may be burdensome for the user. Accordingly, adhesive may be applied to both flaps, thus eliminating the need for ordered folding. Still other means for affixing the flaps in place will occur to those skilled in the art such as, for example, replacing the adhesive system with cohesive material, i.e., material capable of adhering to itself but not to other substrates. In this way both sides of the flap may be coated with cohesive material 34' as illustrated in FIG. 10, and no unique order of folding is required. This also carries the advantage that there is no adhesive applied to the outer crotch portion of the undergarment. In still another embodiment, mating elements of hooks 35 and loops 35', the so-called Velcro binder system (Velcro is a trademark of Velcro USA, Inc.) may be employed. This is illustrated in FIG. 11.

Referring now back to FIGS. 3–5, it will be noted that, as illustrated, the distance between the junction points 45 of the flaps and the absorbent material 30' is approximately the same as the width of the crotch (dimension W). This situation is atypical in that, undergarments as worn, have a wide range of crotch widths varying, for example, from 1.9" to 3.3" inches. A more typical situation is that illustrated in FIGS. 12 and 13 wherein the crotch width W' is substantially greater than the distance between the two junction points 45. Referring first to FIG. 13, illustrated therein schematically, is the application of a napkin 10', to the crotch portion of an undergarment 47. Napkin 10' is similar in every way to napkin 10 with the exception that the flaps 28' of napkin 10' are relatively stiff. Such a condition is found in the prior art as for example in U.S. Pat. No. 4,285,343, issued to Rosetta McNair wherein side flaps are illustrated having a relatively large thickness and provided with a hinge at the junction points of the flaps and the central absorbent body. In this circumstance, when the napkin 46 is emplaced upon the inner crotch portion as in FIG. 3, the flaps are insufficiently drapable to fold about the crotch portion. Instead the flaps fold upon the predetermined hinge, which for napkin 10' is the junction line 45 where a napkin of this configuration is biased to fold. The result is that rather than having the napkin conform to the wider crotch portion, instead the crotch portion is forced to conform to the napkin with the result that the edges 48 of the crotch portion are urged toward the biased junction 45 thereby drawing the edges 48 together and bowing the crotch portion away from the absorbent element 12. It can be seen that when, subsequently, the flaps are brought to overlie the outer crotch portion, because this portion is now bowed, wrinkles and uncertain securement will result. Further, when a so secured napkin is worn, the movements of the wearer will from time to time urge the crotch portion to its full width thereby dislodging or totally disengaging the napkin from its intended position. Needless to say, the effect of bunching the crotch of the undergarment in this manner will also cause discomfort to the wearer of such undergarment.

Figure 12:
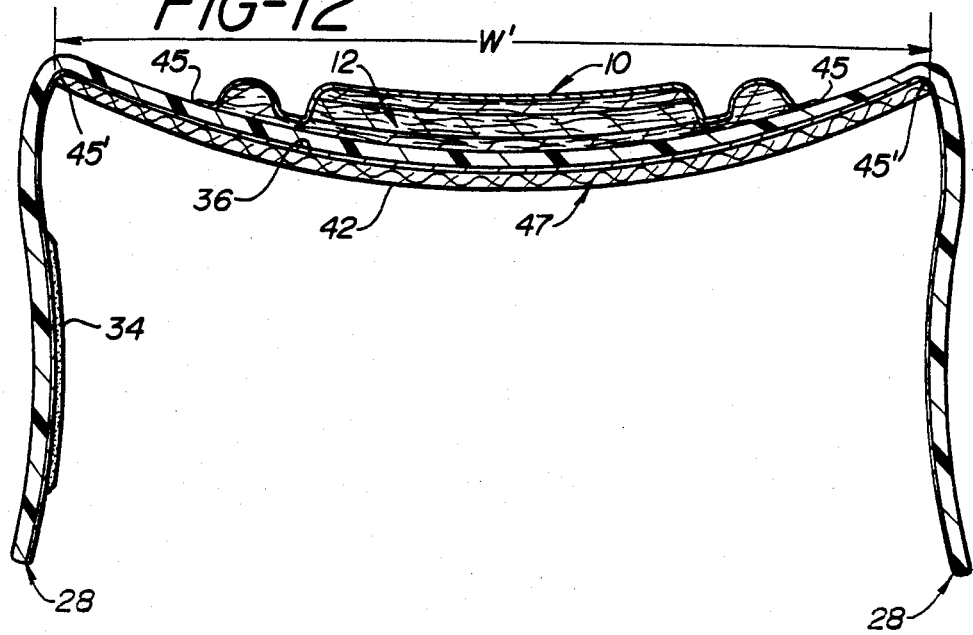
FIG. 12 is a schematic, cross-sectional view of the sanitary napkin of this invention placed onto the inner crotch portion of an undergarment prior to attaching the flaps to the outer crotch portion and illustrating the drapability feature of this invention.
Figure 13:
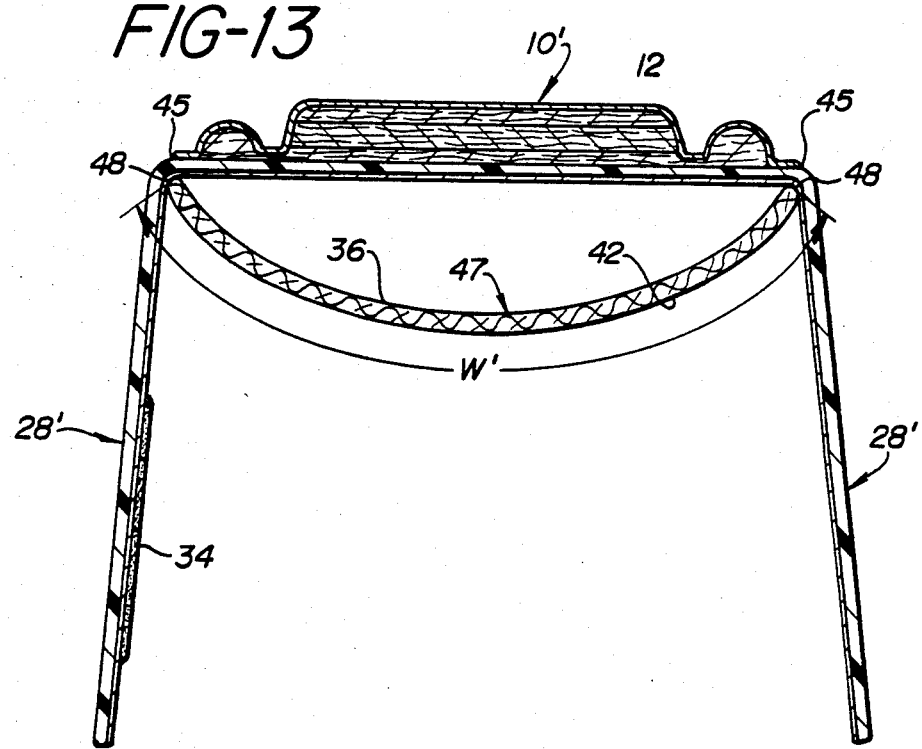
FIG. 13 is a schematic, cross-sectional view of a sanitary napkin, similar to the view illustrated in FIG. 12 but illustrating the disadvantage of a napkin without the drapability feature of this invention.

Referring now to FIG. 12, illustrated therein is the napkin 10 which includes the features of drapable flaps 28. Again, the napkin 10 is emplaced onto the inner crotch portion 36 of the undergarment. Because of its drapability, however, the flaps fold about fold lines 45', these fold lines being dictated by the width of the crotch rather than by each predetermined hinge line in the napkin or flaps. Accordingly, the flaps may now be further folded upon the crotch width dictated fold lines 45' to overlie the outer crotch portion of the undergarment without the concomitant bunching associated with non-drapable flaps illustrated in FIG. 13. It should be understood that fold lines 45' are not unique fold lines and, instead, are one set of an infinite number of lines existing within the drapable flap. The actual fold is determined, in the drapable flap napkin of this invention, by the width of the undergarment crotch as worn by the user. Drapability is accomplished by choosing a material or materials of construction for the flaps which are sufficiently flexible. For example, if the flaps are constructed of polyethylene film having thickness of less than about 5 mils, they will be sufficiently drapable. Preferably, the film should be from 1 to 3 mils thick. In this connection, care should be taken with the choice and disposition of the body fluid absorbing material 30, 30'. For example, if a tissue is employed in conjunction with polyethylene of less than about 5 mils, the flaps will still be flexible enough to have the requisite drapability.

Figure 6:
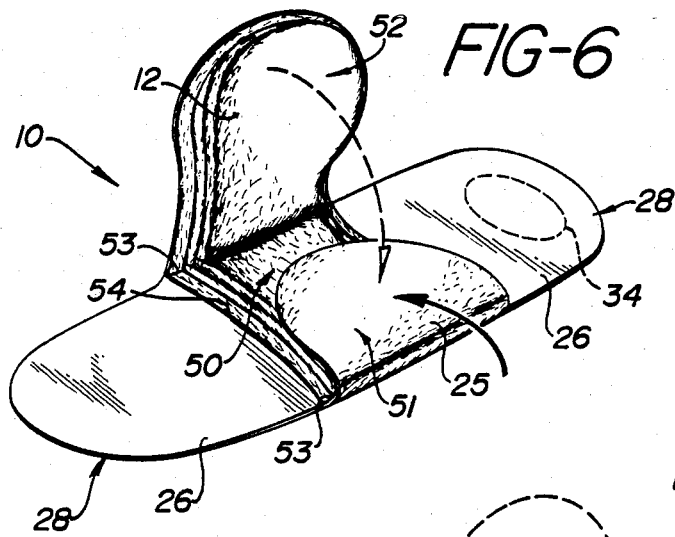
FIG. 6 illustrates first steps in folding the napkin for packaging and disposal.
Figure 7:
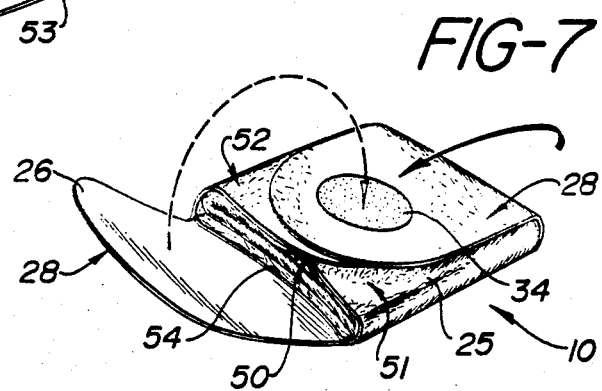
FIG. 7 illustrates further steps in folding the napkin for packaging and disposal.
Figure 8:
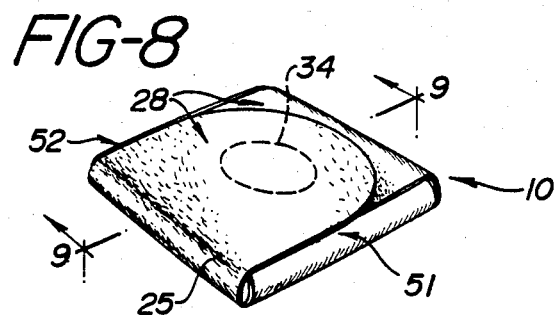
FIG. 8 illustrates the folded napkin.
Figure 9:
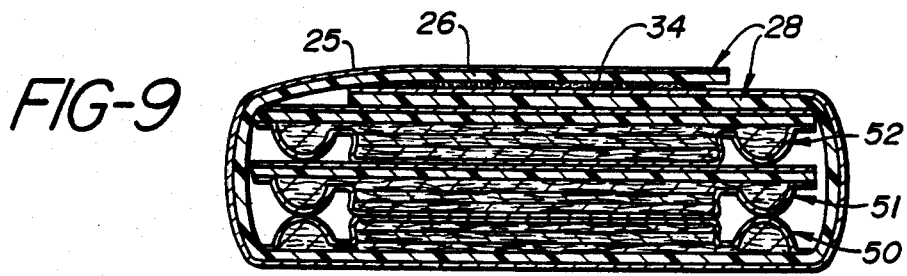
FIG. 9 is a cross-sectional view of the folded napkin taken through line 9—9 of FIG. 8.

Referring now to FIGS. 6–9, illustrated therein is a packaged, folded sanitary napkin 10 and the method for folding same. This method and package may be employed by the manufacturer, in providing the napkin in this form, and by the user, in disposing of the napkin in a hygienic manner. As illustrated in FIG. 6, the central absorbent element 12 is divided longitudinally into three segments, a central segment 50, and two end segments 51 and 52. This division may be by virtue of an actual fold line being impressed into the element 12 by the manufacturer, by a natural bias line occurring at a point 53 where the transverse edges 54 of the flaps are coincident with the element 12 or at an arbitrary fold line selected by the folder. In any event, a first end segment, e.g., end segment 51 is folded upon the central segment 50. The second end segment 52 is then folded over the central segment 50 and, if extensive enough, upon the first end segment 51. Referring to FIG. 7, an adhesive bearing flap 28 is next folded over the first and second end segments 51 and 52 and, finally, referring to FIGS. 8 and 9, the other flap is folded over and adhered to the adhesive bearing flap. As can be seen from FIGS. 8 and 9, the resulting folded napkin presents on its external surface essentially only the garment facing side of the napkin which, of course, is dry and clean after use in that this side has been protected by a body fluid impervious barrier. Thus a used napkin may be hygienically disposed of. Napkins packaged in this manner by the manufacturer or carried by a women in her purse have only the garment facing portion of the napkin exposed and, hence, those portions to be placed in intimate contact with the perineal area of the body are maintained clean.

What is claimed is:

1. In a sanitary napkin of the type for placement in the inner crotch portion of an undergarment, which napkin comprises an absorbent element having a body facing side, a garment facing side, longitudinally extending edges and transverse ends and further comprises flaps extending from each of said longitudinal edges;

the improvement wherein said flaps extend to a length sufficient to allow the flaps to overlie the outer crotch portion of the undergarment, said flaps being sufficiently drapable so as to allow each to fold about said crotch portion at any of the infinite number of lines lying essentially parallel to the junction line between the absorbent element and each flap and the extreme end of said flap, said sufficient drapability being that of a polyethylene film having a thickness of less than about 5 mils;

whereby said sanitary napkin may be applied to crotch portions of varying widths without causing said crotch portions to wrinkle and conform to the dimensions of the sanitary napkin.

2. The sanitary napkin of claim 1 wherein said flaps extend to a length sufficient to allow the flaps to overlap on the outer crotch portion of the undergarment.

3. The sanitary napkin of claim 1 wherein said flaps are provided with means for securement when overlying said outer crotch portion of the undergarment.

4. The sanitary napkin of claim 3 wherein said means comprise pressure sensitive adhesive means.

5. The sanitary napkin of claim 3 wherein said means comprise cohesive means.

6. The sanitary napkin of claim 1 wherein said flaps comprise a barrier material.

7. The sanitary napkin of claim 6 wherein said barrier material comprises polyethylene film having a thickness of about 5 mils or less.

8. The sanitary napkin of claim 1 wherein said flaps in the portion closest to the juncture line of said absorbent element and said flaps comprise absorbent material on the body facing side of said flaps.

9. The sanitary napkin of claim 8 wherein the entire body side of said flaps comprises absorbent material.

10. The sanitary napkin of claim 1 wherein said absorbent element is covered on the garment facing side thereof with a barrier layer and said barrier layer extends from the longitudinal edges to form said flaps.

11. A folded sanitary napkin comprising an absorbent element having a body facing side, a garment facing side, longitudinally extending edges and transverse ends and further comprises flaps extending from each of said longitudinal edges;
said absorbent element being divided by two transverse fold lines into a central segment and first and second end segments;
said first end segment being folded about its adjacent fold line upon the central segment;
said second end segment being folded about its adjacent fold lines over the central segment;
a first of said flaps being folded over the central element; and
the second of said flaps being folded over the central element to complete the folded napkin.

12. The folded napkin of claim 11 wherein said folding is upon the body facing side of said central segment.

13. The sanitary napkin of claim 11 wherein said absorbent element is covered on its garment facing side with a barrier layer and said flaps comprise a barrier material whereby essentially the outer surface of said folded napkin comprises barrier material.

14. The sanitary napkin of claim 11 wherein said first flap comprises securement means on the garment facing side thereof.

15. The sanitary napkin of claim 11 wherein said second flap comprises securement means on the body facing side thereof.

16. A method of folding a sanitary napkin for packaging, storing or disposing of; said napkin being of the type for placement in the inner crotch portion of an undergarment, which napkin comprises an absorbent element having a body facing side, a garment facing side, longitudinally extending edges and transverse ends and further comprises flaps extending from each of said longitudinal edges;
said flaps extending to a length sufficient to allow the flaps to overlie the outer crotch portion of the undergarment; the method comprising the steps:
first folding a first end segment of said absorbent element onto a central segment of said absorbent element about a transverse fold line between said first end segment and said central segment;
then folding a second end segment of said absorbent element over said central segment;
then folding a first of said flap over said central segment; and
then folding a second of said flap over said central segment to produce the folded napkin.

17. The folded napkin of claim 16 wherein the napkin is maintained in the folded position by securing the folded flaps to each other by providing securing means on said first flap.

18. The folded napkin of claim 16 wherein the napkin is maintained in the folded position by securing the folded flaps to each other by providing securing means on said second flap.

* * * * *